United States Patent [19]

Theeten et al.

[11] Patent Number: 4,927,785
[45] Date of Patent: May 22, 1990

[54] METHOD OF MANUFACTURING SEMICONDUCTOR DEVICES

[75] Inventors: Jean-Bernard Theeten, Ozoir-La-Ferriere; Philippe Autier, Paris; Jean Marc Auger, Joinville-Le-Pont, all of France

[73] Assignee: U.S. Philips Corporation, New York, N.Y.

[21] Appl. No.: 201,514

[22] Filed: Jun. 1, 1988

[30] Foreign Application Priority Data

Jun. 4, 1987 [FR] France ................ 87 07796

[51] Int. Cl.$^5$ ............................................. H01L 21/66
[52] U.S. Cl. ................................... 437/225; 437/173
[58] Field of Search ............... 437/225, 228, 173, 174, 437/924; 148/DIG. 102; 250/548

[56] References Cited

U.S. PATENT DOCUMENTS

| | | | |
|---|---|---|---|
| 4,241,109 | 12/1980 | Johnson | 427/162 |
| 4,317,698 | 3/1982 | Christol | 156/650 |
| 4,321,282 | 3/1982 | Johnson | 427/10 |
| 4,326,911 | 4/1982 | Howard | 204/192.32 |
| 4,394,237 | 7/1983 | Donnelly | 204/192.32 |
| 4,454,001 | 6/1984 | Sternheim | 204/192.32 |
| 4,631,416 | 12/1986 | Trutna | 250/548 |
| 4,657,780 | 4/1987 | Pettigrew | 427/162 |
| 4,662,653 | 5/1987 | Greenway | 427/162 |

OTHER PUBLICATIONS

Kleinknecht, "Optical Monitoring...", 5/78, J Electrochem Soc, pp. 798-803.

Primary Examiner—Brian E. Hearn
Assistant Examiner—Kevin McAndrews
Attorney, Agent, or Firm—Paul R. Miller

[57] ABSTRACT

A method of manufacturing semiconductor devices is set forth using reactive ion plasma etching in which an optical grating is formed to etch underlying regions, such as dielectric material, semiconductor material, or alternate layers of different semiconductor material. The optical grating is formed with a rectangular profile having grooves and mask strips on a sample material where each of the grooves has a width $L_S$ substantially equal to the width $L_M$ of the mask strips. The optical grating is formed of a material which may be one of a photoresist, a dielectric compound, a metal, or a metallic compound. This method enables control of reactive ion etching during manufacture of integrated circuits of III-V compounds.

8 Claims, 5 Drawing Sheets

METHOD OF MANUFACTURING SEMICONDUCTOR DEVICES

The invention relates to a method of manufacturing semiconductor devices including at least a reactive ion plasma etching step, which method comprises the steps of:

(a) forming an optical grating having a rectangular profile composed of openings in the form of grooves having a width $L_S$ provided in a layer formed at the surface of the semiconductor material, these openings being parallel and being regularly spaced apart by strips of the material of the layer having a width $L_M$, (b) illuminating the optical grating substantially perpendicularly to its surface with a laser beam having a wavelength $\lambda$ and (c) detecting the light originating from the optical grating.

This method can be used for controlling the process of reactive ion etching of different layers included in the methods of manufacturing integrated semiconductor devices, especially on gallium arsenide (GaAs) or indium phosphide (InP) and generally on III-V compounds.

BACKGROUND OF THE INVENTION

A method as mentioned before is known from the publication of H. P. Kleinknecht and H. Meier in Journal of Electrochemical Society, Vol. 125, No. 5, May 1978, pp. 798 to 803. This document discloses a method wherein the optical grating is composed of openings in the form of grooves provided in a photoresist layer formed on the surface of a dielectric layer of silica (SiO$_2$) or of silicon nitride (Si$_3$N$_4$). The photoresist layer otherwise serves as a mask to obtain by reactive ion etching the etching of patterns into the dielectric layer, which is in turn formed on the surface of a semiconductor substrate of silicon (Si). The grating is intended to control in situ the depth of etching of the dielectric layer by reactive ion plasma etching. For this purpose, the optical grating is illuminated by a laser beam having a wavelength of 632.8 nm, which is modulated and directed substantially perpendicularly to the optical grating arranged in the ion etching structure. The control is effected by the analysis of the light diffracted by the grating. For this purpose, the light intensity originating from the grating is controlled by a photoelectric diode.

The control of the step of etching the dielectric layers is obtained by the interpretation by means of models of the quantitative analysis of the oscillations of the intensity diffracted by the grating. In order to obtain the diffraction conditions, the periodicity of the grating can vary from 3 to 10.2 $\mu$m, the latter value being preferred. The order of diffraction 1 is only considered.

The problem solved by the aforementioned method is the detection of the instant at which the dielectric layer is completely etched and the semiconductor substrate is exposed in order to avoid that the substrate is etched. By measurement of the diffraction intensity, this instant is known by the fact that it coincides with an abrupt diminution of the diffracted intensity, which is then maintained at a low and constant level.

The aforementioned document also indicates that the control of the step of etching the dielectric layers could also be effected by measuring the intensity of the specular reflection. However, in this case, the laser beam would have to be directed to a region of the layer devoid of any irregularity on a surface equally wide as the diameter of the laser beam, which condition can be obtained in practice only with difficulty during the manufacture of integrated circuits on semiconductor substrates. Especially in this case, an optical grating could not be used.

Such a technique utilizes the diffraction of the light. The interpretation is simple in the ideal case of a grating for which only the depth of the etching lines varies, that is to say a model with only 1 parameter. The modellization is very rapidly complexer in the realistic case in which the assembly of the geometry of the grating is modified during the plasma attack. Several parameters act upon the diffracted intensity, of which the contributions practically cannot be separated.

It is especially necessary that not only the thickness of the etched dielectric layers, but also the depth etched into one or several subjacent semiconductor material layers can be measured, as well as the roughness of the etching edges or the roughness of the bottom of the opening etched into the semiconductor material or materials.

These problems are solved by means of the method according to the invention.

SUMMARY OF THE INVENTION

In order to achieve this, a method of the kind described in the opening paragraph is characterized in that the widths $L_S$ and $L_M$ of the grooves and of the spacings of the grating, respectively, are made substantially equal to each other with a dimension larger than the dimension of the coherence zone $l_C$ of the laser beam, in that the layer in which the original grating is formed is made of a material chosen among a photoresist, a dielectric compound, a metal or a metallic compound, and in that the material of which the ion etching must be controlled is chosen among a dielectric compound, a semiconductor compound or an alternation of layers of different semiconductor materials.

By means of the method according to the invention, inter alia the following advantages can be obtained:

the control of the ion etching of three materials can be effected in situ continuously parallel to the etching;

the control of the different parameters in the etching step can be subordinated to this control;

this control provides continuously:

the value of the overall etching depth $d_G$;

the value of the thickness removed at the upper layer of the etched system: $d'_M$;

the thickness of the rough layer on the edges of an etched pattern: $l_F$;

the thickness of the rough layer in the bottom of an etched pattern: $d_R$.

The method according to the invention can readily be carried out and can be operated in a simpler manner than the method to the prior art due to the fact that modulation of the laser beam serving as a source is dispensed with. It is also simpler to obtain gratings of 80 $\mu$m having wide grooves of 40 $\mu$m spaced apart by 40 $\mu$m and without specific precision than gratings having a periodicity of 10.2 $\mu$m having grooves of 7 $\mu$m spaced apart by 3 $\mu$m.

BRIEF DESCRIPTION OF THE DRAWINGS

In order that the invention may be readily carried into effect, it will now be described more fully with reference to the accompanying drawings, in which.

DESCRIPTION OF THE PREFERRED EMBODIMENTS

During the manufacture of integrated circuits on semiconductor substrates, frequently a material is etched by means of a so-called reactive ion etching (R.I.E. = Reactive Ion Etching) method.

Figure 1A:
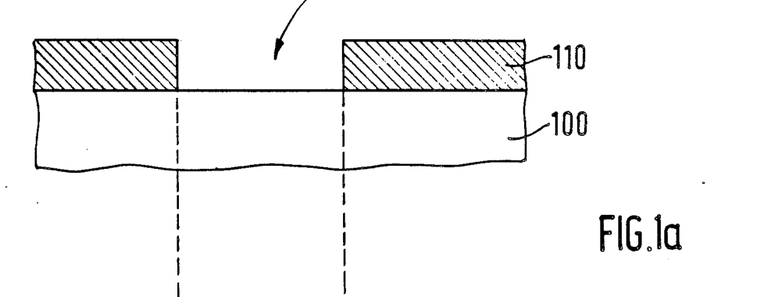
FIGS. 1a and 1b show in sectional view the aspect of a pattern before etching and of a pattern after reactive ion etching, respectively.
Figure 1B:
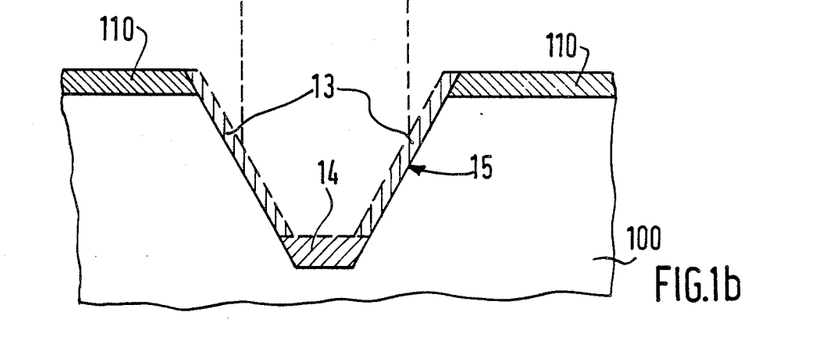

FIGS. 1a and 1b illustrate this method. On a material 100 to be etched, which is considered as the substrate, a layer 110 is deposited to form a mask. Openings or windows 120 are provided in the mask 110, for example by photolithography at the areas chosen for etching of the substrate 100. FIG. 1a shows this substrate in diagrammatic sectional view before reactive ion etching.

FIG. 1b shows diagrammatically in a sectional view corresponding to FIG. 1a the aspect of the opening obtained after etching of the substrate 100 in the prolongation of the opening 120.

The layer 110 forming a mask may be a thin film of an organic material or of a metal or of a dielectric compound, such as silica ($SiO_2$) or silicon nitride ($Si_3N_4$).

The material to be etched at the substrate 100 may be another dielectric compound or a semiconductor compound chosen among the compounds of the group IV or of the group III-V or of the group II-VI. If, for example, the mask consists of silica, the material to be etched may be silicon nitride, or conversely. The semiconductor materials may be silicon, gallium arsenide, gallium aluminium arsenide or indium phosphide, given by way of non-limitative examples.

During the attack by plasma, the ideal behaviour would be that the thin layer serving as a mask is left intact and that the substrate is etched only in the windows while maintaining the geometric relief figure by photolithography, i.e. with vertical attack edges at the boundaries between mask and window. In practice, three parasitic phenomena appear:

(1) The surface 14 of the substrate 100 becomes rough during the attack;

(2) the attack edges 15 are rough and nonvertical, that is to say that a lateral roughness 13 is developed;

(3) the mask 110 itself is attacked and its thickness decreases during the plasma etching step.

According to the invention, these three parasitic phenomena can be limited to a minimum. In fact, since they vary in a complex manner as a function of the microscopic parameters of the plasma (geometry of the electrodes of the plasma, pressure in the plasma chamber, nature and partial pressure of the etching gases, temperature of the sample, nature of the mask used . . .), the optimization is very difficult and time-consuming if no means for rapid and precise characterization are available. The present invention permits providing inter alia a solution for this problem by means of the method described below.

Figure 2:
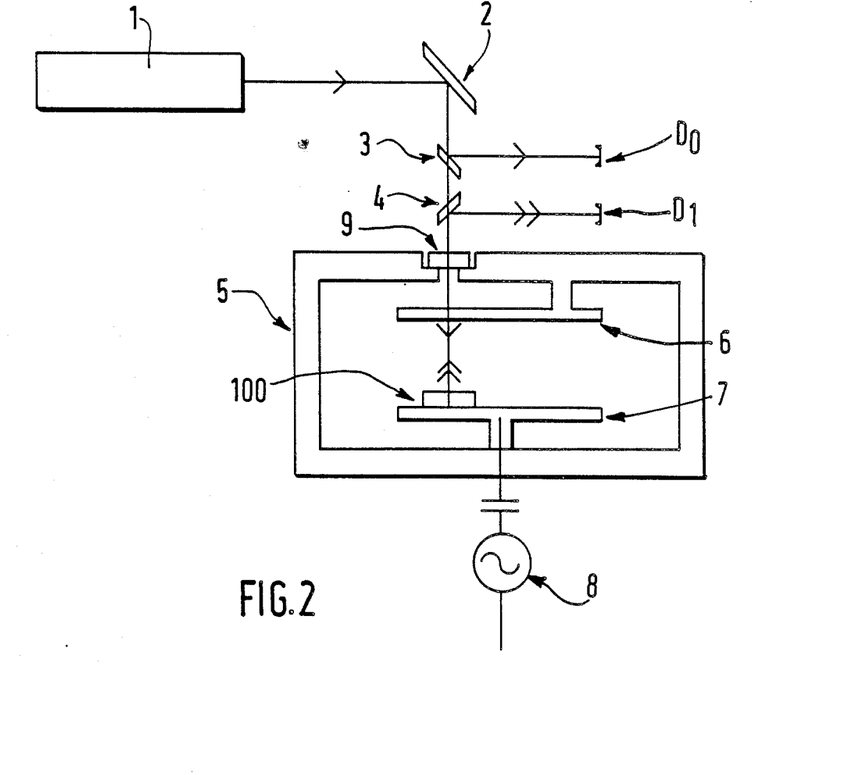
FIG. 2 shows diagrammatically the assembly of the test apparatus according to the invention.

FIG. 2 illustrates diagrammatically an apparatus in which the method according to the invention may be used.

A sample 100 of a material to be etched is disposed in a space 5 on the cathode 7, opposite to the anode 6, between which cathode and anode is established a flow of plasma due to the supply 8, the space moreover being provided with inlets (not shown) for gases, such as $CHF_3$ or $CF_4$, chosen as a function of the material or materials to be etched.

The space 5 is provided with a window 9, to which the beam of a laser 1 is directed by the reflection on the mirror 2. Between the mirror 2 and the window 9, the beam directly originating from the laser is partly reflected by a semi-reflecting plate 3 in the direction of detection means $D_O$, which may advantageously be constituted by a photoelectric diode of silicon, in order to supply a reference signal of the incident intensity.

The beam emitted by the laser is directed to the sample 100 perpendicular to its surface. The surface of the sample which is illuminated by the laser beam has been provided beforehand with an optical grating of the kind described below. This optical grating is arranged to permit not diffraction as known from the prior art, but specular reflection of the laser beam. The light reflected by the optical grating is transmitted through the window 9 and reflected by means of a semi-reflecting plate 4 to a photoelectric diode $D_1$ in order to supply a signal of detection of the intensity reflected by the grating.

The laser beam and the means for detection of the reflected intensity are applied to the space 5 during the entire time of the reactive ion etching operation.

Figure 3A:
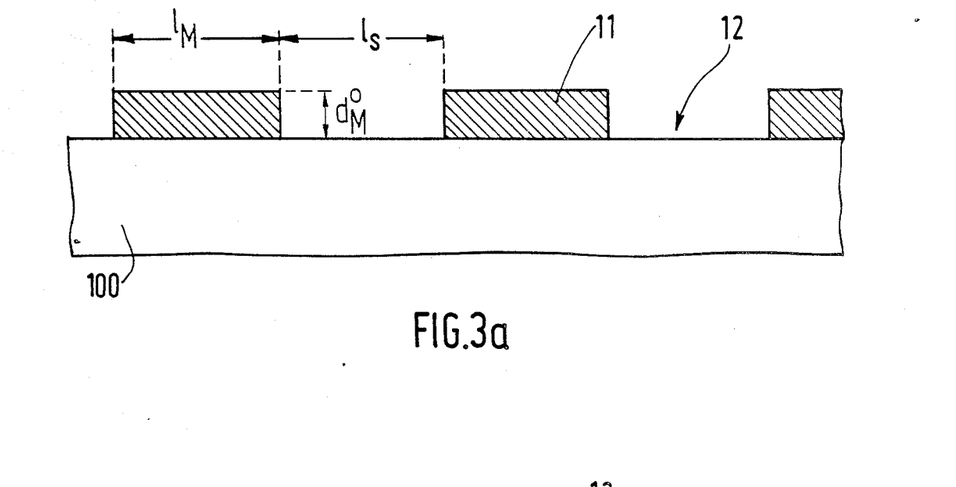
FIG. 3a shows diagrammatically in sectional view the optical grating included in the test apparatus according to the invention and FIG. 3b shows this grating in plan view.
Figure 3B:
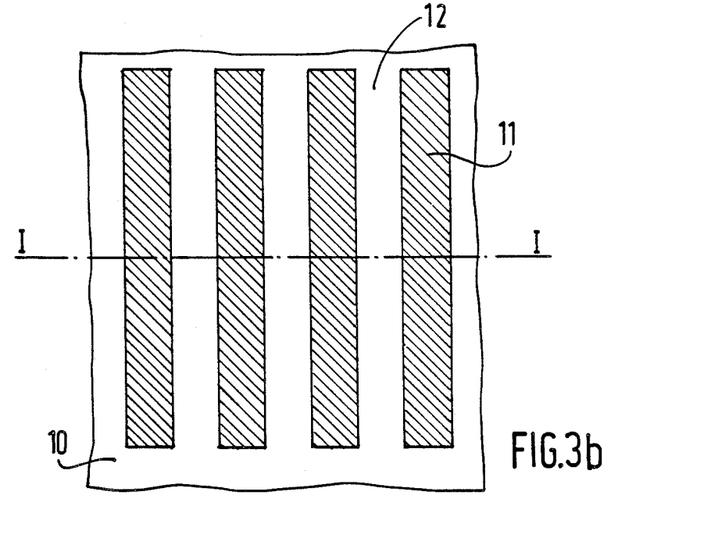

FIG. 3a shows a diagrammatic sectional view taken on the axis I—I of FIG. 3b of the grating used in the method according to the invention.

This grating is formed at the surface of the layer or of the solid material designated as substrate 100 to be etched. It is disposed in a region of the substrate devoid of semiconductor devices during manufacture.

This grating is constituted by openings in the form of grooves 12 provided in a layer of a material 11, which may advantageously be one of the materials mentioned above as suitable to constitute a mask.

As shown in FIG. 3a, the profile of the grating is rectangular. The grooves have a width $l_S$ and are spaced apart by strips of the layer 11 designated as mask strips, which have a width $l_M$. Such a grating can be obtained by a known method of photolithography.

FIG. 3b shows a part of the grating in plan view. The grooves are parallel and are regularly spaced apart.

Advantageously, the grating will cover on the substrate a surface of 1 mm × 1 mm.

In order to permit specular reflection of the laser beam, which is the basis of the advantages obtained by the invention, the widths $l_S$ and $l_M$ will be chosen substantially equal to each other and equal to 40 μm in order to be considerably larger than the dimension of the coherence zone $l_C$ or the laser beam, whose wavelength $\lambda$ is chosen to be 628.3 nm, which is obtained by means of a He-Ne-laser.

The coherence zone is defined as being the zone within which two points are always sufficiently close to each other to interfere with each other.

The coherence length of the laser beam is then a constant of the optical system and is:

$$l_C = 20\ \mu m.$$

A method of determining the dimension of the coherence zone of such an optical system will be described in detail below.

Thus, regions of the grating mutually separated by more than 20 μm return light beams without relative phase coherence and whose intensities are added to each other and no longer return the amplitudes, according to the prior art. This property permits decoupling the respective contributions of the various mechanisms evoked above:

(1) rate of etching the substrate ($V_S$),
(2) rate of etching the mask ($V_M$),
(3) lateral roughness ($r_L$),
(4) roughness of the substrate ($r_S$).

Figure 4:
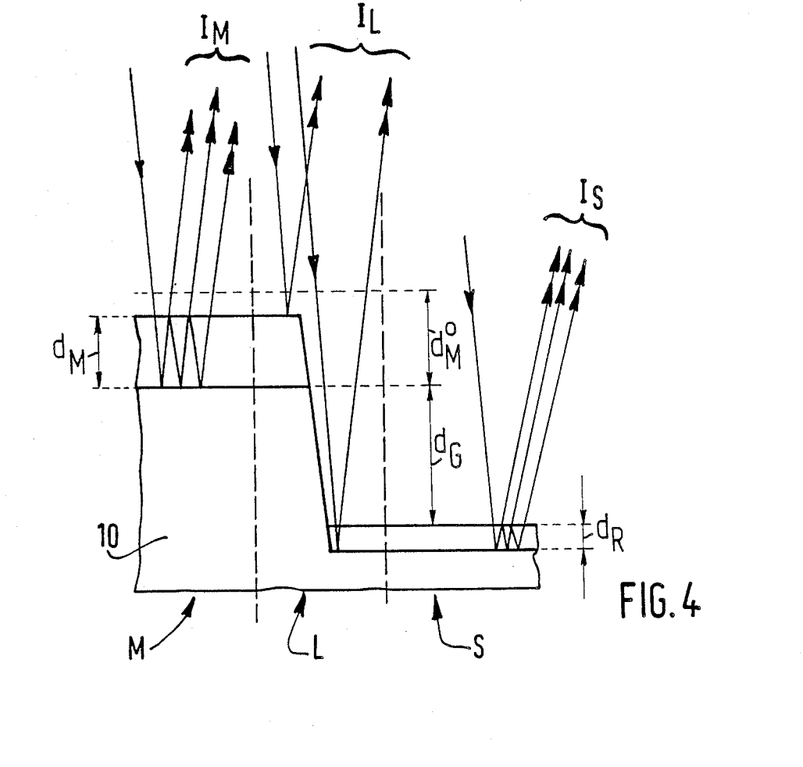
FIG. 4 shows in sectional view the path of the rays of the laser beam incident and reflected by the grating.

The choice of $l_S = l_M = 40\ \mu m$ is a compromise based on the fact that:

(1) this dimension is larger than the coherence dimension of the laser to permit separated contributions of the mask strips 11 and of the grooves 12;

(2) this dimension is fairly small in order that the regions at the boundaries between strip and groove provide a further substantial contribution to the global reflection signal. The importance of such a pattern can be seen when a typical situation is examined during etching, as shown in FIG. 4.

Three types of regions can be distinguished which contribute to the specular reflection of the laser beam.

The regions M of the mask strip 11 situated at more than a coherence dimension from a boundary between mask strip and groove correspond to the multiple interferences in the thin film having a thickness $d_M$, which constitute the strips 11 before etching. For incidence of the laser beam normal to the surface, the amplitude reflected by a region M is given by the relation:

$$A_M = \frac{r_{AM} + r_{MS} \cdot \exp(-j\phi_M)}{1 + r_{AM} \cdot r_{MS} \cdot \exp(-j\phi_M)}$$

where
$r_{AM}$ is the Fresnel coefficient at the interface air/mask strip,
$r_{MS}$ is the Fresnel coefficient at the interface mask strip/substrate, $$\phi_M = 2 \cdot \frac{2\pi}{\lambda} \cdot n_M \cdot d_M,$$

wherein $n_M$ is the optical index of the material of the strip at the wavelength λ of the laser and $d_M$ is the thickness of this mask strip during etching.

Likewise, the regions S of the substrate situated at more than a coherence length from a boundary between strip and groove correspond to the multiple interferences in the thin film having a thickness $d_R$ of the roughness of the substrate developed during the plasma attack. The amplitude reflected by these regions is given by the relation:

$$A_S = \frac{r_{AR} + r_{RS} \cdot \exp(-j\phi_R)}{1 + r_{AR} \cdot r_{AS} \cdot \exp(-j\phi_R)}$$

where
$r_{AR}$ is the Fresnel coefficient at the interface air/roughness,
$r_{RS}$ is the Fresnel coefficient at the interface roughness/substrate, $$\phi_R = 2 \cdot \frac{2\pi}{\lambda} \cdot n_R \cdot d_R,$$

where $n_R$ is the optical index of the film of roughness and where $d_R$ is the thickness of the rough layer.

Finally, the regions L situated at the boundaries between mask strip and groove and having a width $l_C$ equal to the coherence dimension of the laser light correspond to the interference between the high and the low part of the patterns during etching. If $d_G$ represents the thickness etched into the substrate, i.e. the difference in height between the interface substrate/strip and the interface air/roughness of the substrate, the contribution in reflected amplitude of these regions L is given by the relation:

$$A_L = A_M + A_S \cdot \exp(-j\phi_G)$$

with $$\phi_G = 2 \cdot \frac{2\pi}{\lambda} \cdot d_G.$$

It is essential to note that due to the normal incidence of the laser light the vertical or non-vertical edges of the pattern at the boundary between strip and groove do not contribute to the specularly reflected amplitude. During etching, these edges occupy a width $l_F$ and the regions L therefore have a contribution proportional to $l_C - l_F$.

The respective proportions of three types of regions M, S and L are therefore:
$l'_M$, $l'_S$ and $2l_C$
with $l'_M + l'_S + 2l_C = l_M + l_S$
and $l'_M = l'_S$.

During etching, the global reflected intensity is therefore given by the relation:

$$I = \frac{l'_M \cdot |A_M|^2 + l'_S \cdot |A_S|^2 + 2(l_C - l_F) \cdot |A_L|^2}{l_M + l_S}$$

where the quantities varying during a plasma attack are therefore in decreasing order of importance:
the etched thickness $d_G$ acting upon $A_L$,
the residual thickness of the mask $d_M$ acting upon $A_M$ and $A_L$,
the lateral dimension $l_F$ of the etching edges,
the roughness of the substrate $d_R$ acting upon $A_S$ and $A_L$.

The importance of the present invention is that the contributions of these four quantities are separable and that their four values can be obtained from the only measurement in course of time of the intensity of the specular reflection.

Figure 5A:
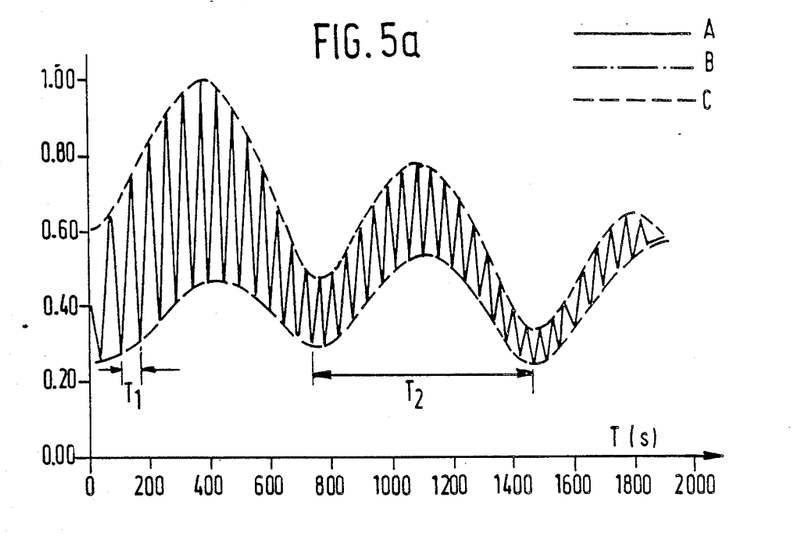
FIG. 5a shows the curve of the light intensity reflected by the grating as a function of the etching time when the grating is formed on a substrate of gallium arsenide.

A typical use of this method is now described, which corresponds to the measurement of the intensity of the specular reflection given in FIG. 5a. A step of reactive ion etching of a (100) orientated GaAs substrate in a commercially available assembly (NEXTRAL NE 110 C structure) is concerned. The experimental conditions were as follows:

overall pressure 3 mtorr,
power RF=70 W (self-polarization voltage 250 V), partial pressures of the gases
$Cl_2$=4.5,
$CH_4$=4.5,
$Ar$=9.

FIG. 5a shows that the reflected intensity I varies with the time t in accordance with a sinusoidal line having a short period $T_1$ (between two minima) illustrated by the full line A. The amplitude of the curve A is moreover decreasing. This curve admits two envelopes: the envelope B of the minima, which is a sinusoidal line having a period $T_2$ long with respect to $T_1$ ($T_2$ being chosen between 2 minima) and the envelope C of the maxima, which is also a sinusoidal line having a period $T_2$, but whose amplitude is decreasing.

The short period $T_1$ corresponds in the term $A_L$ to the variation of $d_G$. Each time period $T_1$ corresponds to an etching depth:

$$P_1 = \lambda/2 \cdot n_o = \lambda/2,$$

where $n_o$ is the index of air ($n_o$=1).

If the ion etching step begins at the instant $t_o$ there will be etched at the end $$d_G = N_1 P_1 + (n_M - n_o)(d_M^o - d_M)$$

where $P_1 = N_1 \lambda/2$, $n_o = 1$ and where $N_1$ is the number of periods $T_1$ appearing between the instant $t_o$ and the instant $t_1$.

Thus, the evaluation of the etched depth can be effected permanently during the whole time of the etching operation.

In the example mentioned, where $\lambda = 632.8$ nm, $T_1$ corresponds to $P_1 \simeq 316$ nm of etched material.

The long period $T_2$ corresponds to the depth $P_2$ etched superficially into the mask strips of the grating:

$$P_2 = \lambda/2 n_M,$$

where $n_M$ is the index of the material of the strips of the grating. If the strips of the grating consist of silica ($SiO_2$) having an index $$n \simeq 1.53,$$

$T_2$ corresponds to $P_2 = 205$ nm of etched silica.

At the end of an instant $t_1$, the etching will have reduced the thickness of the mask strips of the grating by a value $$(n_M - n_o)(d_M^o - d_M) = N_2 P_2 \text{ where } P_2 = \lambda/2 \, n_M,$$
$$n_o = 1 \text{ and}$$

where $N_2$ is the number of periods $T_2$ appearing between the instant $t_o$ and the instant $t_1$.

The thickness of the substrate 100 really etched will be given by $d_G = (N_1 \lambda/2) + (N_2 \lambda/2 n_M)$ $$d_G = N_1 P_1 + N_2 P_2.$$

The diminution of the amplitude of the sinusoidal line A having a short period is solely due to the lateral roughness $l_F$. FIG. 5a shows that $l_F$ practically reaches $l_C$ at the end of a time t=2000 s. (that is to say an amplitude zero of the contribution $(l_C - l_F) |A_L|^2$). Now, for a sacrificed pilot sample subjected to such an etching step, the roughness measured by a scanning electron microscope is $$l_F = 20 \, \mu m,$$

which permits deducing that the value of the coherence dimension $l_C$ of the optical system according to the invention is $l_C = 20 \, \mu m$.

At any instant t, the lateral dimension $l_F$ of the etching edges can then be deduced from the curves of FIG. 5a. In fact, the value $l_F - l_C$ is proportional to the difference in amplitude between the curve B and the curve C, which can be written as:

$$l_F - l_C = K \cdot \Delta A.$$

The proportionality constant K is determined by modellization taking into account the fact that, when the difference between the amplitude $\Delta A$ is a maximum, the dimension $l_F$ is a minimum or zero ($l_F \simeq 0$).

Finally, the roughness $d_R$ of the bottom of the grooves after etching at an instant t can be determined by the modellization of the decrease of the minimum intensity of the curve B (lower envelope), which modellization takes into account the fact that the roughness can be simulated by a layer having an effective refractive index lying between that of air and that of the substrate. This modellization can be effected by measuring the thickness of the roughness $d_R$ of one or several reference samples. This measurement can be obtained by spectroscopic ellipsometry, which method is known from European patent application EP-A No. 87201918 and European patent application EP-A No. 87201919.

It can be noted that the curve B of FIG. 5a does not show a substantial decrease, which results from the fact that the etching conditions are satisfactory and that only an extremely small roughness occurs at the bottom of the groove. In this case, the thickness of the roughness $d_R$ at the bottom of the grooves has been estimated at 10 nm.

Figure 5B:
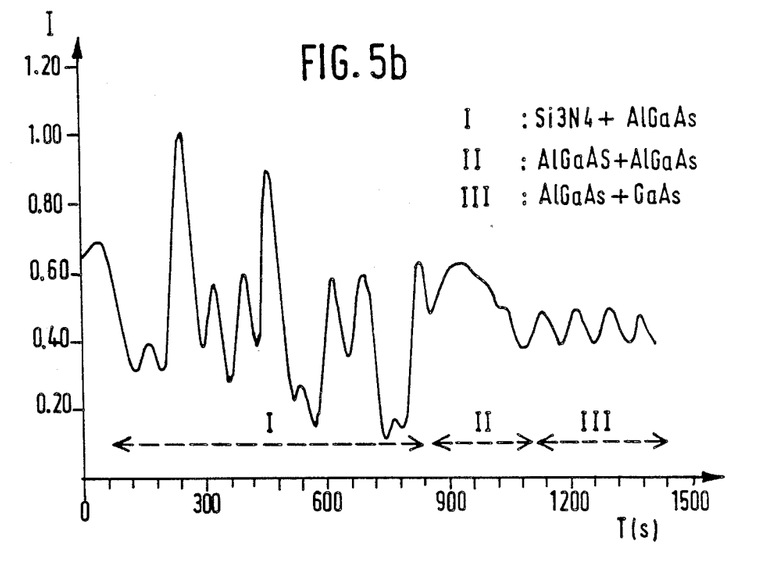
FIG. 5b shows the curve of the light intensity reflected by the grating as a function of the etching time when the grating is formed in a silicon nitride ($Si_3N_4$) layer at the surface of a thin gallium aluminium arsenide layer deposited on a gallium arsenide substrate.

FIG. 5b shows the curve of intensity reflected by a grating, whose strips consist of silicon nitride $Si_3N_4$) formed on a substrate constituted by a thin layer of gallium aluminium arsenide (GaAlAs) formed at a surface of gallium arsenide (GaAs). A simple examination of the ruptures of the inclination of the curve I as a function of time permits detecting:

the end of the step of etching $Si_3N_4$,
the end of the step of etching AlGaAs in the grooves.

The step of reactive ion etching of the dielectric layers has been effected by means of $CHF_3$ or $CF_4$ gas and the step of reactive ion etching of the semiconductor compounds has been effected by means of $Cl_2$, $CH_4$, Ar gases.

The region II corresponds to the etching of AlGaAs only and the region III corresponds to the etching of AlGaAs and GaAs.

The advantage of the method according to the invention is therefore the direct real time determination of the 4 parameters $d_G$, $d_M$, $l_F$ and $d_R$. The conventional technique in this field, which was known hitherto from the prior art, was the examination a posteriori with a scanning electron microscope of cloven sections of the sample. Besides the destructive and long characters of this method, it had the disadvantage that it only gives the final state after etching without providing access to the dynamic range of the phenomena. On the contrary, the method according to the invention:

provides in real time the evolutions of $d_G$, $d_M$, $l_F$ and $d_R$;

permits rapidly detecting the poor operating conditions (more particularly the case in which $d_R$ and $l_F$ are high), can be interpreted by direct reading of the evolution I as a function of the time t in the case in which $d_M << d_G$;

is satisfactorily adapted to the complex situation in which the "substrate" is constituted by several successive thin layers.

What is claimed is:

1. In a method of manufacturing semiconductor devices using reactive ion plasma etching which method comprises the steps of
   (a) forming an optical grating having a rectangular profile of grooves and mask strips on a sample material, each of said grooves having a width $L_s$ and each of said mask strips having a width $L_m$, where $L_s$ is substantially equal to $L_m$, said optical grating being formed of a material selected from one of a photoresist, a dielectric compound, a metal, or a metallic compound, and said sample material being formed of a material selected from one of a dielectric compound, a semiconductor compound, or alternate layers of different semiconductor material;
   (b) illuminating said optical grating substantially perpendicularly to a surface of said optical grating with a laser beam, said laser beam having a wavelength $\lambda$, said widths $L_s$ and $L_m$ being larger in dimension than a dimension lc of the coherence zone of said laser beam;
   (c) detecting specular reflection of said laser beam being reflected from said optical grating; and
   (d) reactive ion etching said sample material through said optical grating.

2. A method according to claim 1, wherein said width $L_s$ and said width $L_m$ are each equal to 40 μm.

3. A method according to claim 1 or claim 2, wherein said wavelength $\lambda$ of said laser beam is 632.8 nm.

4. A method according to claim 1 or claim 2, wherein said sample material is formed of a III-V group semiconductor compound.

5. A method according to claim 4, wherein said III-V group semiconductor compound is one of gallium arsenide (GaAs), gallium aluminum arsenide (GaAlAs), or indium phosphide (InP), and wherein said material of said optical grating is one of silica ($SiO_2$) or silicon nitride ($Si_3N_4$).

6. A method according to claim 1 or claim 2, wherein when said step (d) of reactive ion etching is carried out, intensity of said reflected laser beam is measured as a first periodical curve of decreasing amplitude having a short period $T_1$ between two minima of said first periodical curve, and is measured as a second periodical curve of decreasing amplitude having a long period $T_2$ between two minima of a lower envelope of said first periodical curve, said second periodical curve being formed of said lower envelope and an upper envelope, wherein said first periodical curve is formed between said lower envelope and said upper envelope, and wherein said step (d) is begun at a time $t_o$ and stopped at a time $t_1$, said time $t_1$ being a function of data derived from said first and second periodical curves, wherein said data includes
   (A) an overall depth $d_G$ etched into said sample material given by the relation $d_G = N_1 P_1 + N_2 P_2$ between $t_o$ and $t_1$, where $N_1$ is the number of short periods between $t_o$ and $t_1$, $P_1 = \lambda/2n_o$, where $n_o$ is the refractive index of air, $N_2$ is the number of long periods between $t_o$ and $t_1$, and $P_2 = \lambda 2n_m$ where $n_m$ is the index of refraction of said material of said optical grating;
   (B) a lateral dimension of $l_f$ of etching edges of said sample material given by the relation $l_f - l_c = K \times$ difference of amplitudes at time t between said lower envelope and said upper envelope, where K is a constant determined by modellization, where $l_f = 0$ where the difference of the amplitudes is a maximum, and $l_f = l_c$ when said difference of the amplitudes is zero; and
   (C) a thickness $d_R$ of roughness at the bottom of an etched groove given at said time t by the modellization of the decrease of minimum intensity of said lower envelope, said modellization resulting from simulation by a layer having an effective refractive index between that of air and that of said sample material.

7. A method according to claim 6, wherein measurement of said lateral dimension $l_f$ at said etching edges at said time t is effected by measuring in a scanning electron microscope the lateral dimension $l'_f$ of edges of a reference sample material under conditions $l_f = l_c$ which is a constant of said optical grating.

8. A method according to claim 7, wherein said modellization for determining said thickness $d_R$ is effected by measuring with spectroscopic ellipsometry a thickness of roughness $d'_R$ of said reference sample material.

* * * * *